United States Patent
Novikov et al.

(10) Patent No.: US 10,849,528 B2
(45) Date of Patent: Dec. 1, 2020

(54) COMPUTER-ACCESSIBLE MEDIUM FOR DETERMINING ARTERIAL INPUT FUNCTION

(71) Applicants: New York University, New York, NY (US); Albert-Ludwigs-Universitat Freiburg, Freiburg (DE)

(72) Inventors: Dmitry Novikov, New York, NY (US); Jerian Jahani, Brooklyn, NY (US); Valeriji G. Kiselev, Freiburg (DE)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/574,474

(22) PCT Filed: May 16, 2016

(86) PCT No.: PCT/US2016/032756
§ 371 (c)(1),
(2) Date: Nov. 15, 2017

(87) PCT Pub. No.: WO2016/187146
PCT Pub. Date: Nov. 24, 2016

(65) Prior Publication Data
US 2018/0140217 A1    May 24, 2018

Related U.S. Application Data

(60) Provisional application No. 62/162,242, filed on May 15, 2015.

(51) Int. Cl.
| | | |
|---|---|---|
| *A61B 5/055* | (2006.01) | |
| *A61B 5/0275* | (2006.01) | |
| *G01R 33/563* | (2006.01) | |
| *A61B 5/00* | (2006.01) | |
| *A61B 5/026* | (2006.01) | |
| *A61B 8/06* | (2006.01) | |
| *A61B 5/029* | (2006.01) | |

(52) U.S. Cl.
CPC ............. *A61B 5/055* (2013.01); *A61B 5/00* (2013.01); *A61B 5/0042* (2013.01); *A61B 5/026* (2013.01);
(Continued)

(58) Field of Classification Search
CPC ......... A61B 5/0042; A61B 5/00; A61B 5/026; A61B 2576/026; A61B 5/029; G01R 33/56366
See application file for complete search history.

(56) References Cited

U.S. PATENT DOCUMENTS

| | | | |
|---|---|---|---|
| 2003/0045791 A1 | 3/2003 | Carroll | |
| 2009/0297008 A1 | 12/2009 | Taxt et al. | |
| 2012/0095328 A1* | 4/2012 | Lee | A61B 5/02755 600/420 |

FOREIGN PATENT DOCUMENTS

DE    102011084867 B4    7/2014

OTHER PUBLICATIONS

Konstas et al. 2009 Am. J. Neuroradiol. 30:662-668.*
(Continued)

*Primary Examiner* — Keith M Raymond
*Assistant Examiner* — Patrick M Mehl
(74) *Attorney, Agent, or Firm* — Hunton AK LLP

(57) ABSTRACT

An exemplary system, method and computer-accessible medium for determining an arterial input function (AIF) of a mammal(s) can be provided, which can include, for example, receiving information related to a global circulatory system of the mammal(s), and determining the AIF based on the information by modeling a blood flow in the global circulatory system of the mammal(s) in terms of an input response function(s). The input response function(s) can include a delayed input response function(s). In certain exemplary embodiments of the present disclosure, the input
(Continued)

response function(s) can include at least three input response functions, and each of the input response functions can be from a different part of a body of the mammal(s). The AIF can be determined by coupling the input response functions. The AIF can be further determined based on a total tracer amount in an organ(s) of the mammal(s).

36 Claims, 5 Drawing Sheets

(52) U.S. Cl.
CPC ............ *A61B 5/0275* (2013.01); *A61B 8/065* (2013.01); *G01R 33/56366* (2013.01); *A61B 5/029* (2013.01); *A61B 2576/026* (2013.01); *G01R 33/563* (2013.01)

(56) References Cited

OTHER PUBLICATIONS

Calamante 2013 Progress in Nuclear Magnetic Resonance Spectroscopy 74:1-32.*
Calamante et al. 2004 Magnetic Resonance in Medicine 52:789-797.*
Ostergaard 2005 J. Mag. Reson. Imag. 22:710-717 (Year: 2005).*
Zhang et al. 2009 J. Magn. Reson. Imaging 30:656-665 (Year: 2009).*
Jahani et al. 2014 Proc. Intl. Soc. Mag. Reson. Med. 22:4598 (Year: 2014).*
Zierler, Kenneth, "Indicator Dilution Methods for Measuring Blood Flow, Volume, and Other Properties of Biological Systems: a Brief History and Memoir," Annals of Biomedical Engineering, vol. 28, pp. 836-848, 2000.
Kellner, Elias et al., "Quantitative Cerebral Blood Flow with Bolus Tracking Perfusion MRI: Measurements in Porcine Model and Comparison . . . ," Magnetic Resonance in Medicine, vol. 72, pp. 1723-1734, 2014.
Yablonskiy, Dmitriy A. et al., "Probing Lung Microstructure with Hyperpolarized Noble Gas Diffusion MRI: Theoretical Models and Experimental Results," Magnetic Resonance in Medicine, vol. 71, pp. 486-505, 2014.
Calamanta, T., "Arterial Input Function in Perfusion MRI: a Comprehensive Review," Progress in Nuclear Magnetic Resonance Magnetic Resonance Spectroscopy, pp. 1-32, 2013.
International Search Report and Written Opinion dated Sep. 9, 2016 for International Application No. PCT/US2016/032756.

* cited by examiner

COMPUTER-ACCESSIBLE MEDIUM FOR DETERMINING ARTERIAL INPUT FUNCTION

CROSS REFERENCE TO RELATED APPLICATIONS

This application relates to and claims the benefit and priority from International Patent Application No. PCT/US2016/032756 filed on May 16, 2016, which relates to and claims priority from U.S. Provisional Patent Application Ser. No. 62/162,242, filed on May 16, 2015, the entire disclosures of which are incorporated herein by reference.

FIELD OF THE DISCLOSURE

The present disclosure relates generally to determination(s) of arterial input function ("AIF") and blood volume ("BV") and more specifically, to exemplary embodiments of exemplary systems, methods and computer-accessible medium for determining AIF and absolute BV from global recirculation.

BACKGROUND INFORMATION

Indicator-dilution techniques have been developed since the early 19th century. Today, they are primary tools in different modalities of in vivo medical imaging, including positron emission tomography, computed tomography and magnetic resonance imaging. These techniques can be used to estimate tissue characteristics (e.g., regional blood volume and flow that can serve as disease biomarkers). Available tracer kinetic models do not account for tracer recirculation, which is the major feature of blood circulation. Tracer transport in an organ of interest is treated as if the organ is part of an open pipeline in which the input is independent of the output. To conform the measured tracer amount to such models, the first passage of tracer through the organ is extracted from the more feature-rich data. Beyond the information loss, isolating the first passage from the successive overlapping boluses can lead to biases. One major bias is in the estimation of local blood volume, which is given by the area under the single bolus in the single-pass picture. This area, which diverges due to recirculation, is usually found by employing an ad hoc cut-off.

Thus, it may be beneficial to provide an exemplary system, method and computer-accessible medium for determining AIF and absolute BV from global recirculation, which can overcome some deficiencies present in current systems for determining AIF and BV.

SUMMARY OF EXEMPLARY EMBODIMENTS

To that end, exemplary systems, methods and computer-accessible medium can be provided for determining an arterial input function ("AIF"), which can be a time-resolved concentration of a blood tracer of any kind (e.g., either exogenous, such as, but not limited to, relaxation-enhancing or X-ray absorbing contrast agent or a radioactive tracer, and/or endogenous such as, but not limited to, for example, nuclear magnetic resonance-labeled spin magnetization), of a mammal(s) (e.g., a body part of a mammal) can be provided, which can include, for example, receiving information related to a global circulatory system of the mammal(s), and determining the AIF based on the information by modeling a blood flow in the global circulatory system of the mammal(s) in terms of an input response function(s) of, for example, part(s) of the mammal's body. The input response function(s) can include a delayed and/or dispersed input response function(s). In certain exemplary embodiments of the present disclosure, the input response function(s) can include at least three input response functions, and each of the input response functions can be from a different part of a body of the mammal(s). The AIF can be determined by coupling the input response functions. The AIF can be further determined based on a total tracer amount in an organ(s) of the mammal(s). The total tracer amount can be obtained by summing the tracer amount for each voxel in a plurality of voxels in image(s) of the organ(s). The information can be received from a magnetic resonance imaging apparatus(es), a computed tomography apparatus(es) or a positron emission tomography apparatus(es).

Additionally, an exemplary system, method and computer-accessible medium for determining a blood volume ("Bv") of an organ(s) of a mammal(s), can be provided, which can include, for example receiving information related to (i) an arterial input function ("AIF") of the organ(s) including a recirculation effect and (ii) a local tissue tracer concentration of the organ(s) including the recirculation effect, and determining the BV based on a ratio of an integrated local tissue concentration and an integrated AIF. Both the numerator and the denominator of the ratio can be integrated up to a time limit, which can be based on a particular time where the ratio can stop significantly varying.

In some exemplary embodiments of the present disclosure, the AIF can be determined by receiving further information related to a global circulatory system of the mammal(s), and determining the first information based on the further information by modeling a blood flow in the global circulatory system of the mammal(s) as an input response function(s).

In some exemplary embodiments of the present disclosure, the tracer concentration can be found for each imaging apparatus(es) (e.g., magnetic resonance imaging apparatus(es), a computed tomography apparatus(es) or a positron emission tomography apparatus(es)) in a method-specific way. For example, for the magnetic resonance imaging apparatus, the total tracer amount can be obtained by summing a relaxation rate for each voxel in a plurality of voxels in image(s) of the organ(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 2A:
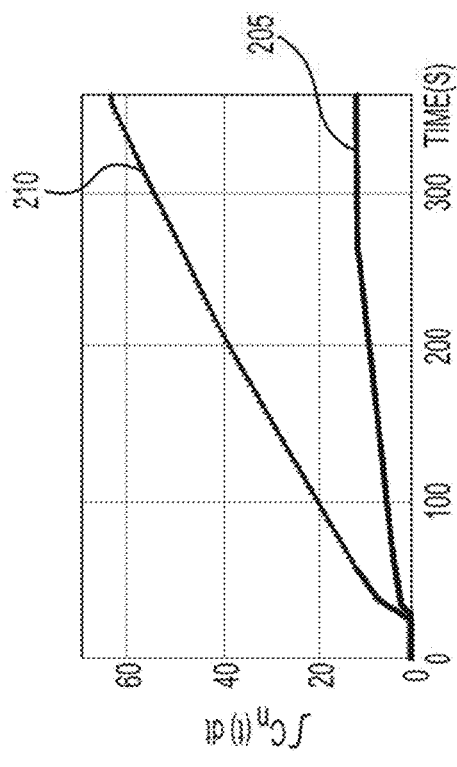
Figure 2B:
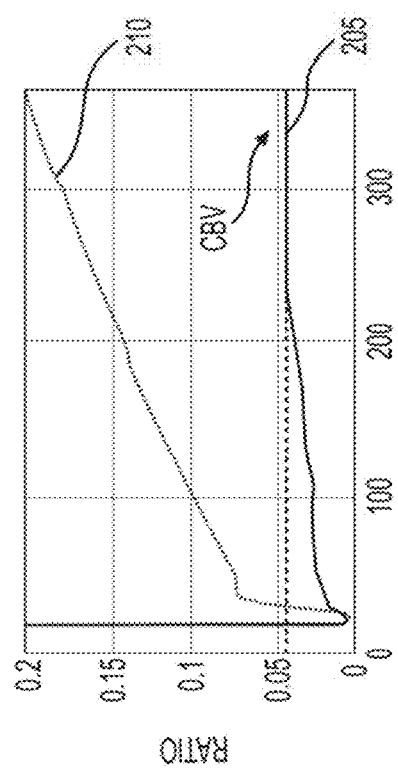
Figure 2C:
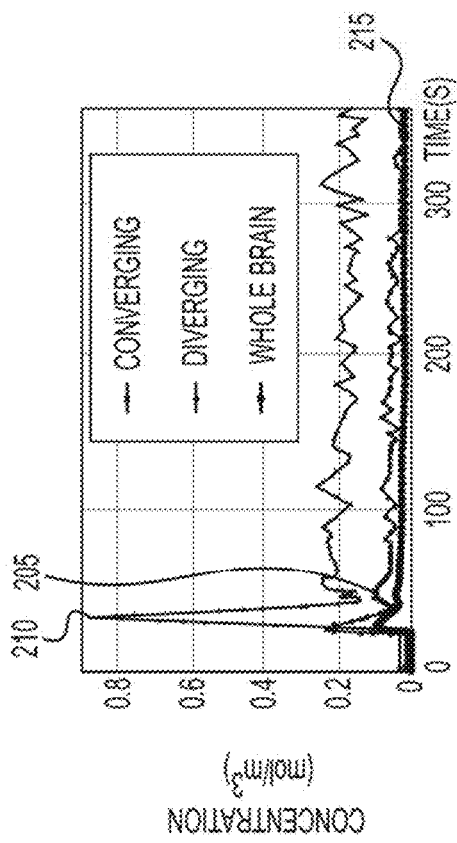
Figure 2D:
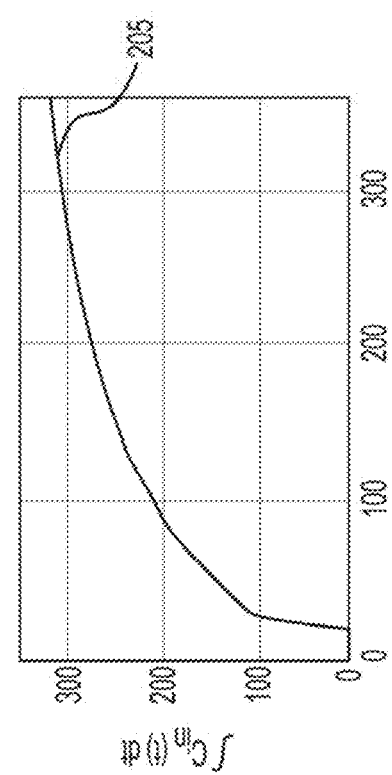
Figures 3A, 3B:
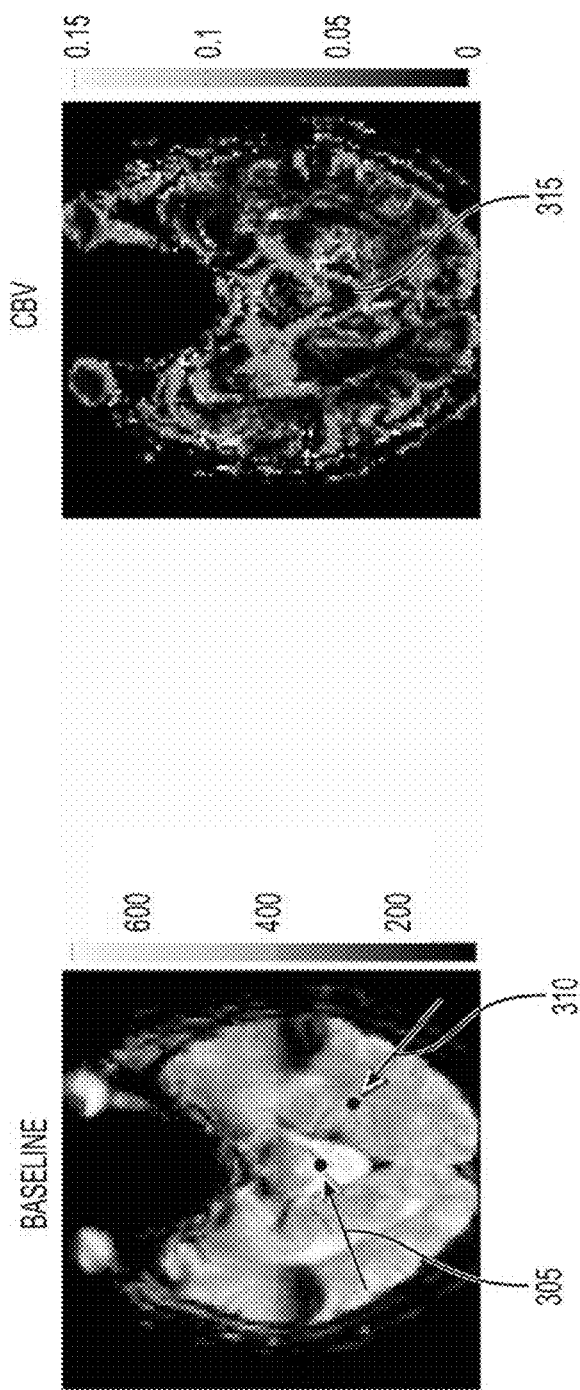
Figure 4:
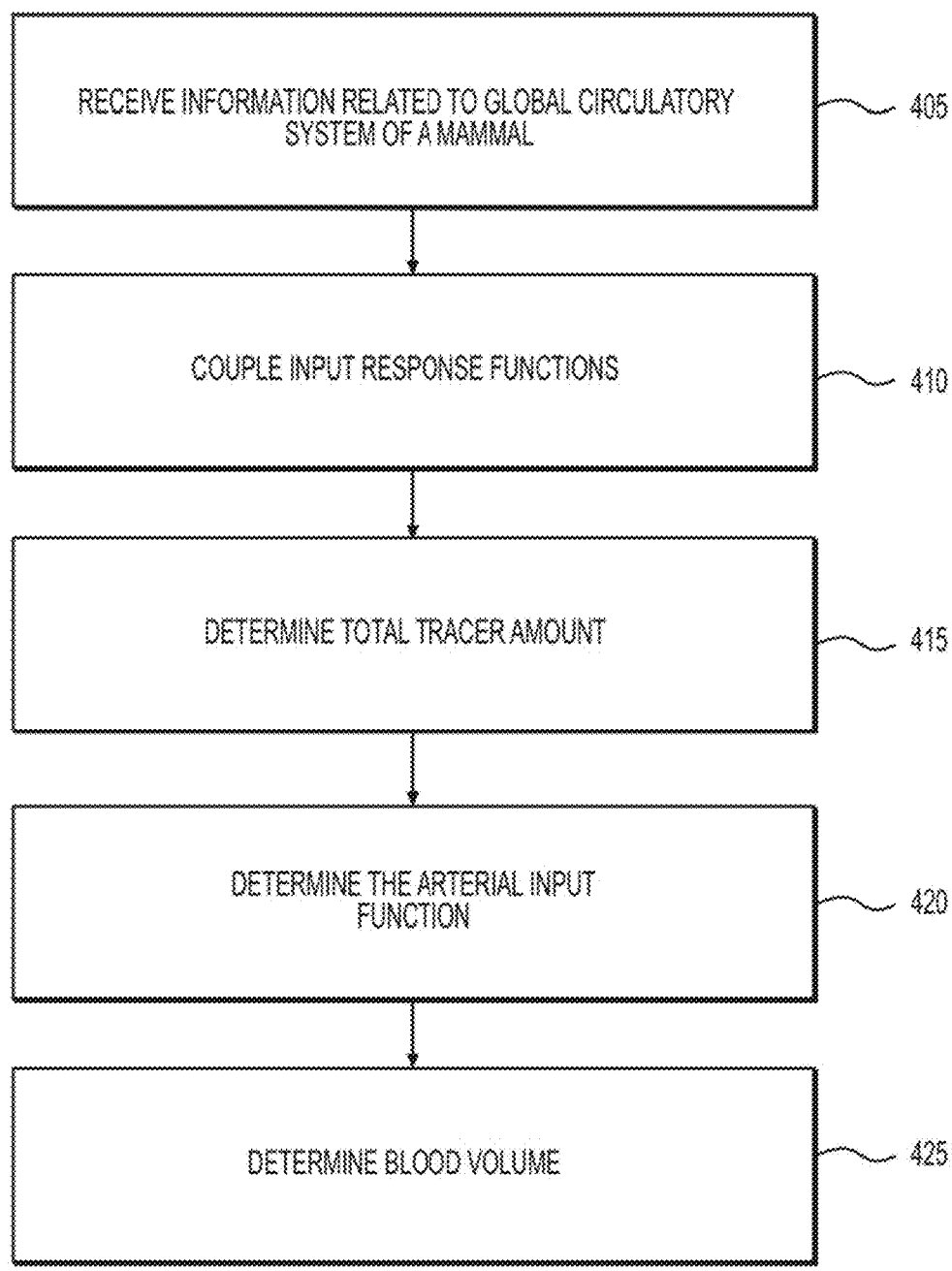
Figure 5:
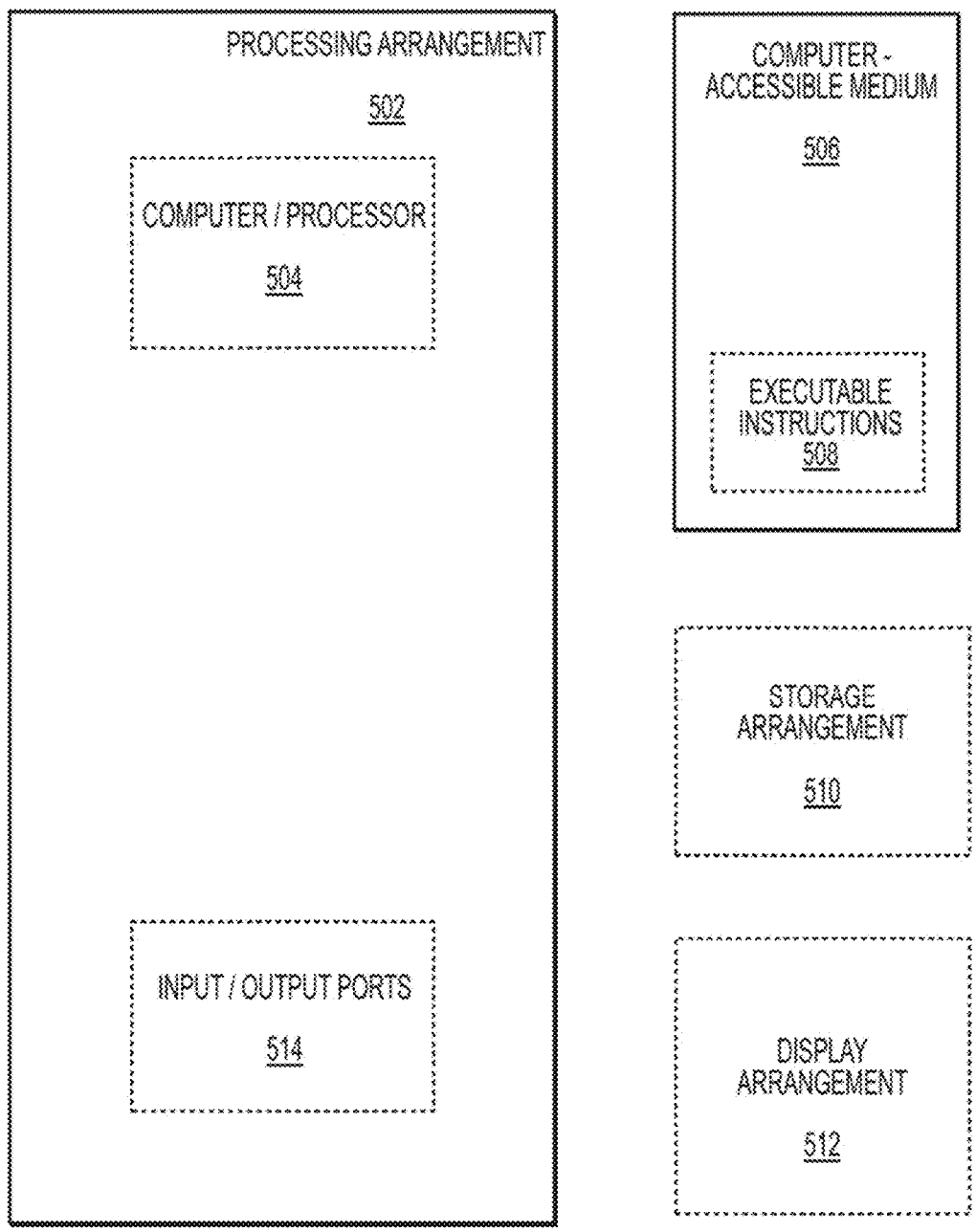

Figures is a graph illustrating tracer concentrations utilized and/or obtained with the exemplary system, method and computer-accessible medium according to an exemplary embodiment of the present disclosure;

FIGS. 2B and 2C are graphs illustrating the integral of the tracer concentrations from FIG. 2A according to an exemplary embodiment of the present disclosure;

FIG. 2D is a graph illustrating the ratio of the integrals from FIGS. 2B and 2C according to an exemplary embodiment of the present disclosure;

FIGS. 3A and 3B are exemplary images illustrating the localization of voxels from the tracer concentrations from the graph shown in FIG. 2A according to an exemplary embodiment of the present disclosure;

FIG. 4 is a flow diagram of an exemplary method for determining an arterial input function (AIF) and a blood volume BV of at least one mammal according to an exemplary embodiment of the present disclosure; and FIG. 5 is an illustration of an exemplary block diagram of an exemplary system in accordance with certain exemplary embodiments of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method and computer-accessible medium can be used to estimate absolute blood volume ("By"), which is the local blood volume fraction in a given tissue, and the arterial input function(s) ("AIF") of individual organ(s), without the need for direct physical AIF measurement. BV can provide a valuable diagnostic contrast. However, thus far, only relative BV has been estimated, which can be BV defined relative to different locations, without being able to obtain absolute BV values. The parameter, BV, can rely on the fundamental quantity, (e.g., AIF), whose direct measurement can be challenging. (See, e.g., References 1, 2 and 5.) Furthermore, AIF estimation has relied on the first bolus passage, which can be inaccurate, as the first pass, and subsequent recirculation boluses, can overlap. The global recirculation framework can be used for determining AIF, which can include all recirculation boluses, and which can further facilitate the estimation of the BV. The exemplary biomarker (e.g., the absolute BV) can be beneficial, for instance, for the detection and the grading of tumors, as well as in strokes and in neurodegenerative diseases.

Exemplary Method and Procedure

Figure 1A:
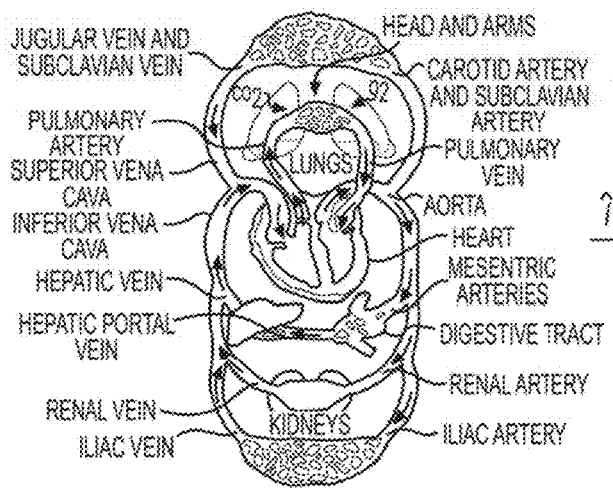
FIG. 1A is a diagram illustrating veins and arteries of a mammal (e.g. a human)
Figure 1B:
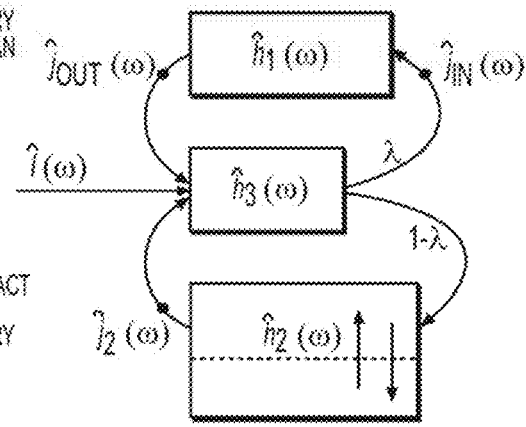
FIG. 1B is a state diagram associated with the diagram of FIG. 1A according to an exemplary embodiment of the present disclosure.

AIF estimation has been a century-old problem. Technically, AIF estimation uses modeling recirculation as opposed to a single pass of tracer through an organ. To resolve this problem, the global circulatory system can be considered (see, e.g., diagram shown in FIG. 1A), and the blood flow can be modeled by multiple appropriately delayed, or dispersed, impulse response functions ("IRF"s) $h_i(\omega)$ as shown in the state diagram of FIG. 1B (e.g., three IRFs). The tracer kinetics by the IRFs can be presented in the Fourier domain, where convolutions can turn into products. Thus, for example:

$$j_{out}(\omega)=h_1(\omega)j_{in}(\omega), j_{in}(\omega)=\lambda h_3(\omega)[I(\omega)+j_{out}(\omega)+j_2(\omega)]$$

$$j_2(\omega)=(1-\lambda)h_2(\omega)h_3(\omega)[I(\omega)+j_{out}(\omega)+j_2(\omega)] \quad (1)$$

Eq. (1) can be valid for any injection profile $I(\omega)$, which can often be a rectangular pulse produced in accordance with, for example, magnetic resonance ("MR") or computed tomography ("CT") tracer injection protocols). The coupling between IRFs from different parts of the body can facilitate adequate description of recirculation. Eq. (1) can be solved exactly, and the influx $j_{in}(\omega)$ in an organ can be obtain as, for example:

$$\hat{j}_{in}(\omega) = \frac{\hat{I}(\omega)\lambda\hat{h}_3(\omega)}{1-\lambda\hat{h}_3(\omega)\hat{h}_1(\omega)-(1-\lambda)\hat{h}_3(\omega)\hat{h}_2(\omega)} \quad (2)$$

Eq. (2) can yield the tracer influx to, for example, the brain, where λ can be the fraction of blood going to the brain. The corresponding time-domain expression for the influx of tracer in this organ (e.g., the brain) can be obtained using, for example, an inverse Fourier transform of $j_{in}(\omega)$, which can be performed either numerically, or analytically using particular functional forms for the IRFs $h_i$, i=1, 2, 3, and employing, for example, methods of integration over the complex plane of w. Such exemplary IRFs can have, but are not limited to, the form of the gamma-variate probability distribution function. The exemplary denominator of Eq. (2) can include the effects of global recirculation; expanding the inverse of this denominator as a geometric series can yield subsequent recirculation boluses. The pole(s) at low frequency ω in the lower half plane of the complex-valued ω (e.g., the zeroes of the denominator in Eq. (2)) can yield the steady-state influx, and the approach to the steady-state.

The net amount $M_1(\omega)$ of tracer in a given organ (e.g., the brain) can be related to the influx $j_{in}(\omega)$ via the residue function $R_1(\omega)=[1-h_1(\omega)]/(-i\omega):M_1(\omega)=R_1(\omega) j_{in}(\omega)$. This relation, Fourier transformed (e.g., either analytically or numerically, as described above) to the time domain, can relate the time course of the influx into a given organ (e.g. the brain) to the net tracer amount $M_1(t)$ at any moment of time t, including all recirculation effects. It can be the net amount $M_1(t)$ that can be measured, using, for example, CT, magnetic resonance imaging ("MM") and/or positron emission tomography ("PET"). Thus, the above relations can facilitate the determination of the parameters of the IRFs $h_i$, i=1, 2, 3, and thereby the parameters of Eq. (2) for the influx $j_{in}(\omega)$ and its time course $j_{in}(t)$, using, for example, nonlinear fitting.

Figure 1C:
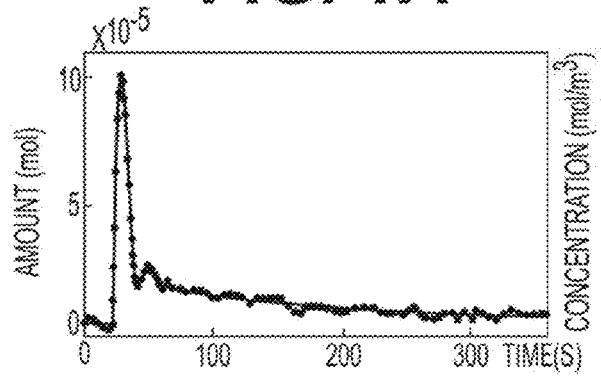
FIGS. 1C and 1D are graphs illustrating exemplary results produced by the exemplary system, method and computer-accessible medium according to an exemplary embodiment of the present disclosure.

In particular, for the exemplary MRI perfusion applications, the exemplary system, method and computer-accessible medium, according to an exemplary embodiment of the present disclosure, can also be used to determine the net amount $M_1(t)$ from the mapping of the local tissue tracer concentration $c_n^{tis}(t)=\zeta_n c_n(t)$ in any organ (e.g., the brain), where n=1, . . . , and can refer to a given voxel, and N can be the number of all voxels. Here, $c_n(t)$ can be the tracer concentration in the blood within a given $n^{th}$ voxel, and $\zeta_n$ can be the BV in this voxel. The net amount $M_1(t)$ can be found from the map of the dynamic susceptibility contrast ("DSC") MRI signal $S_n(t)$, acquired over the whole organ (e.g., the brain), and it can have exceptionally low noise (see e.g., exemplary graph of FIG. 1C), as it can be averaged over $N \sim 10^5$ or even more voxels, in the following exemplary manner: $M_1(t)$ can be proportional to the average of ln S(t) over the brain. Thus, for example:

$$S_n(t) = S_{0,n} e^{-\Delta R_{2,n}^*(t) T_E}, \sum_{n=1}^{N} \Delta R_{2,n}^*(t) = \Omega \sum_{n=1}^{N} \zeta_n c_n(t) = \Omega \frac{M(t)}{V_v} \quad (3)$$

Figure 1D:
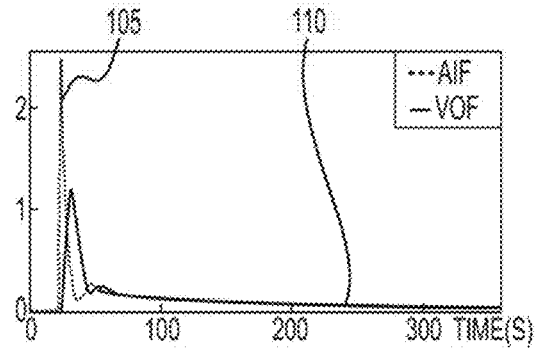

Here $S_{0,n}$ can be the pre-bolus signal and $T_E$ can be echo time. The transverse relaxation rate in the nth voxel $\Delta R_{2,n}^*(t)$, which can be determined from the MRI signal using any suitable procedure, can be expressed in terms of the tissue tracer concentration $c_n^{tis}(t) = m_n(t)/V_v$, which can be the product of the blood concentration $c_n(t) = m_n(t)/v_n$ of contrast agent, and of the volume fraction $\zeta_n = v_n/V_v$ of blood in that voxel, or the BV. (See e.g., Reference 3). The voxel volume, $V_v$, and the proportionality constant, $\Omega = \chi \gamma B_0/3$, can be known, while the volume $v_n$ of vasculature can cancel. Eq. (3) can provide a procedure to determine the net amount $M_1(t) = M(t)$ of tracer in an organ (e.g. the brain) by summing the logarithm of the DSC MRI signal over all, or most, of the imaging voxels, and by multiplying this sum by a particular (e.g., known) coefficient. Summing over the logarithm of the signal, rather than over the signal itself, can be beneficial for DSC MRI, as compared to other exemplary imaging modalities. The knowledge of $M_1(t)$ can facilitate the nonlinear parameter estimation for the IRFs $h_i$, i=1, 2, 3, and thus for the AIF. FIG. 1D illustrates a graph of the estimated AIF (e.g., line 105) and the venous output function ("VOF") (e.g., line 110).

Using the estimated IRF parameters, AIF can be obtained as $c_{in}(\omega) = j_{in}(\omega)/F_{in}$, and subsequently transformed into the time domain using various exemplary procedures of complex integration. The blood inflow into the brain, $F_{in} = \lambda F_c$, can be the fraction A of cardiac output $F_c$, which can be presumed to be known from a separate and standard measurement (e.g., the average human cardiac output $F_c = 8 \times 10^{-5}$ m$^3$/s).

BV, defined as the voxel-wise fraction $\zeta_n$ of blood (e.g., cerebral blood volume ("CBV"), for the case of brain) in a voxel n in the presence of recirculation effects can be determined as the ratio of the two diverging integrals (e.g., as functions of the upper limit T). Thus, for example:

$$\zeta_n = \lim_{T \to \infty} \frac{\int_0^T c_n^{tis}(t) dt}{\int_0^T AIF(t) dt} \quad (4)$$

where the numerator can be the integrated local tissue concentration measured with any imaging modality (e.g., MRI, PET and CT), and the denominator can be the integrated AIF(t)=$c_{in}(t)$, either measured at the entrance of the organ, or quantified as described above based on the net amount $M_1(t)$ in the organ.

FIG. 2A shows an exemplary graph illustrating the tracer concentration in two voxels, converging (e.g., line 205) and diverging (e.g., line 210), as well as the whole brain (e.g., line 215). FIGS. 2B and 2C show exemplary graphs illustrating how the integrals of AIF and voxel concentrations diverge.

Both the numerator and the denominator of Eq. (4) can diverge due to recirculation, but their ratio can converge. (See e.g., graph shown in FIG. 2D). This definition can resolve the common issue of having to isolate the first bolus, and can provide a procedure for determining the BV in the case of recirculation, without the need to isolate the first bolus. The ability to correctly determine BV in the presence of the recirculation effects can rely on the global AIF, $c_{in}(t)$ for the organ, which can also include the recirculation effects, which can compensate for the divergence in the numerator of Eq. (4). This can provide the desired connection between the fundamental problem of recirculation and the clinically valuable contrast provided by BV.

Exemplary MM Experiments

Informed consent was obtained from a glioma patient. Gradient echo images were acquired during Gd-DTPA administration (e.g., 0.1 mM/kg, 5 mL/s) at is intervals for first 60 s, and at 5 s intervals for next 300 s totaling 120 samples. Imaging was performed on a 3T Siemens whole body scanner with an 8-channel phased array head coil. Parameters: TR=1000 ms, TE=32 ms, 10 contiguous 3 mm thick axial slices, matrix 128×128, FOV=220×220 mm$^2$, FA=30°, BW=1396 Hz/pixel, in-plane resolution 1.7×1.7 mm$^2$.

Exemplary Results

Figure 1E:
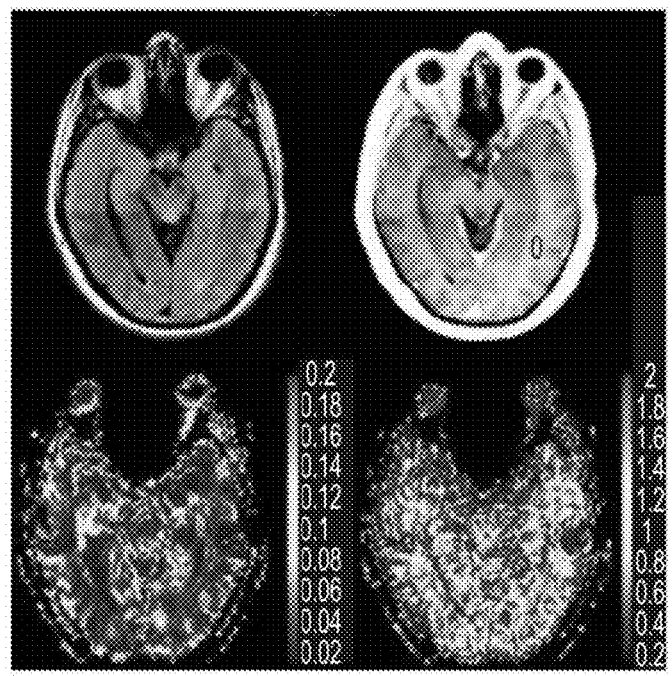
FIG. 1E is a set of exemplary images of the brain according to an exemplary embodiment of the present disclosure.

Compared to the relative cerebral BV ("rCBV") (see e.g., exemplary images in FIG. 1E), the exemplary system, method and computer-accessible medium, according to an exemplary embodiment of the present disclosure, can determine the absolute measure of CBV. A small fraction of voxels with a diverging ratio in Eq. (4) (see e.g., exemplary images of FIGS. 3A and 3B) can correspond to imaging artifacts, regions of high blood volume and tracer leakage at tumor edge, where relations between the signal and the CBV can break down. (See, e.g., Reference 2). For example, FIG. 3A shows an exemplary image having marked voxels 305, 310, and FIG. 3B shows an exemplary image that illustrates diverging voxels (e.g., mostly artifacts). (See, e.g., element 315 of FIG. 3B).

Exemplary Description

The exemplary system, method and computer-accessible medium, according to an exemplary embodiment of the present disclosure, can link the tracer kinetics in a particular organ to the topology in the whole body. Thus, the exemplary system, method and computer-accessible medium, according to an exemplary embodiment of the present disclosure, can generalize the formula for the regional BV to incorporate the whole tracer concentration time course, which can release the current restriction to its first pass. The exemplary system, method and computer-accessible medium can be applied in a technically feasible DSC MRI study for a glioma patient. The exemplary global framework can provide the basis for quantitative perfusion studies using MM, PET and CT procedure.

FIG. 4 shows a flow diagram of an exemplary method 400 for determining an arterial input function and a blood volume of a mammal according to an exemplary embodiment of the present disclosure. For example, at procedure 405, information related to a global circulatory system of the mammal can be received. The information can be coupled to one or more input response functions as procedure 410, and the total tracer amount (e.g., a tracer amount) can be determined at procedure 415. At procedure 420, the arterial input function for the mammal can be determined, which can then be used to determine the total blood volume of the mammal at procedure 425.

FIG. 5 shows a block diagram of an exemplary embodiment of a system according to the present disclosure. For example, exemplary procedures in accordance with the present disclosure described herein can be performed by a processing arrangement and/or a computing arrangement 502. Such processing/computing arrangement 502 can be, for example entirely or a part of, or include, but not limited to, a computer/processor 504 that can include, for example one or more microprocessors, and use instructions stored on a computer-accessible medium (e.g., RAM, ROM, hard drive, or other storage device).

As shown in FIG. 5, for example a computer-accessible medium 506 (e.g., as described herein above, a storage device such as a hard disk, floppy disk, memory stick, CD-ROM, RAM, ROM, etc., or a collection thereof) can be provided (e.g., in communication with the processing arrangement 502). The computer-accessible medium 506 can contain executable instructions 508 thereon. In addition or alternatively, a storage arrangement 510 can be provided separately from the computer-accessible medium 506, which can provide the instructions to the processing arrangement 502 so as to configure the processing arrangement to execute certain exemplary procedures, processes and methods, as described herein above, for example.

Further, the exemplary processing arrangement 502 can be provided with or include an input/output arrangement 514, which can include, for example a wired network, a wireless network, the internet, an intranet, a data collection probe, a sensor, etc. As shown in FIG. 5, the exemplary processing arrangement 502 can be in communication with an exemplary display arrangement 512, which, according to certain exemplary embodiments of the present disclosure, can be a touch-screen configured for inputting information to the processing arrangement in addition to outputting information from the processing arrangement, for example. Further, the exemplary display 512 and/or a storage arrangement 510 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, those having ordinary skill in the art should understand as. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:
1. Kellner E. MRM 2013.
2, Kellner E. MRM 2013.
3. Yablonskiy D. MRM 1994.
4. Zierler K. Ann Biomed Eng. 2000.
5. German Patent No. 102011 084867

What is claimed is:

1. A non-transitory computer-accessible medium having stored thereon computer-executable instructions for determining circulatory information regarding at least one organ of at least one mammal, wherein, when a computer arrangement executes the instructions, the computer arrangement is configured to perform procedures comprising:
generating at least one magnetic resonance imaging (MRI) pulse;
applying the at least one MRI pulse to at least one portion of the at least one mammal;
receiving at least one imaging signal from the at least one mammal that is based on the at least one MRI pulse;
determining a local tissue tracer concentration of the at least one organ using the at least one imaging signal received from the at least one mammal, wherein the local tissue tracer concentration is based on a recirculation effect in the at least one organ;
determining at least one impulse response function (IRF) based on the local tissue tracer concentration;
determining an arterial input function (AIF) using the at least one IRF; and
determining the circulatory information based on a ratio of an integrated local tissue tracer concentration and an integrated AIF.

2. The non-transitory computer-accessible medium of claim 1, wherein a numerator and a denominator of the ratio are integrated up to a time limit.

3. The non-transitory computer-accessible medium of claim 2, wherein the time limit is determined based on a particular time where the ratio stops significantly varying.

4. The non-transitory computer-accessible medium of claim 1, wherein the computer arrangement is further configured to determine the AIF by:
receiving a patient-specific tracer tissue concentration time course related to a global circulatory system of the at least one mammal; and
determining the AIF based on the patient-specific tracer tissue concentration time course by modeling a blood circulation in the global circulatory system of the at least one mammal as at least one input response function.

5. The non-transitory computer-accessible medium of claim 1, wherein the at least one organ is a brain of the at least one mammal.

6. The non-transitory computer-accessible medium of claim 1, wherein the computer arrangement is configured to determine the at least one IRF based on a non-linear parameter estimation of the local tissue tracer concentration.

7. The non-transitory computer-accessible medium of claim 1, wherein the at least one imaging signal is a dynamic susceptibility contrast (DSC) MRI signal, and wherein the computer arrangement is configured to determine the local tissue tracer concentration using at least one map of the DSC MRI signal.

8. The non-transitory computer-accessible medium of claim 7, wherein the computer arrangement is configured to determine the local tissue tracer concentration at least one of (i) by at least one of summing a logarithm of the DSC MRI signal over at least a portion of imaging voxels generated using the DSC MRI signal or (ii) using a lookup table.

9. The non-transitory computer-accessible medium of claim 1, wherein the computer arrangement is configured to determine the AIF based on the at least one IRF by:
determining an influx into the at least one organ based on the at least one IRF, and
determining a cardiac output of the at least one mammal.

10. The non-transitory computer-accessible medium of claim 9, wherein the computer arrangement is configured to determine the AIF based on the at least one IRF by:
   determining a blood flow into the at least one organ based on the cardiac output, and
   determining a ratio between the influx and the blood flow.

11. The non-transitory computer-accessible medium of claim 1, wherein the computer arrangement is configured to determine the at least one IRF based on the local tissue concentration by integrating the local tissue concentration across voxels of the at least one portion.

12. The non-transitory computer-accessible medium of claim 1, wherein the circulatory information includes at least one of (i) a blood volume of the at least one organ or (ii) a blood flow of the at least one organ.

13. A system for determining circulatory information regarding at least one organ of at least one mammal, comprising:
   a computer hardware arrangement configured to:
      generate at least one magnetic resonance imaging (MRI) pulse;
      apply the at least one MRI pulse to at least one portion of the at least one mammal;
      receive at least one imaging signal from the at least one mammal that is based on the at least one MRI pulse;
      determine a local tissue tracer concentration of the at least one organ using the at least one imaging signal received from the at least one mammal, wherein the local tissue tracer concentration is based on a recirculation effect in the at least one organ;
      determine at least one impulse response function (IRF) based on the local tissue tracer concentration;
      determine an arterial input function (AIF) using the at least one IRF; and
      determine the circulatory information based on a ratio of an integrated local tissue tracer concentration and an integrated AIF.

14. The system of claim 13, wherein a numerator and a denominator of the ratio are integrated up to a time limit.

15. The system of claim 14, wherein the time limit is determined based on a particular time where the ratio stops significantly varying.

16. The system of claim 13, wherein the computer hardware arrangement is further configured to determine the AIF by:
   receiving a patient-specific tracer tissue concentration time course related to a global circulatory system of the at least one mammal; and
   determining the AIF based on the patient-specific tracer tissue concentration time course by modeling a blood circulation in the global circulatory system of the at least one mammal as at least one input response function.

17. The system of claim 13, wherein the at least one organ is a brain of the at least one mammal.

18. The system of claim 13, wherein the computer hardware arrangement is configured to determine the at least one IRF based on a non-linear parameter estimation of the local tissue tracer concentration.

19. The system of claim 13, wherein the at least one imaging signal is a dynamic susceptibility contrast (DSC) MRI signal, and wherein the computer hardware arrangement is configured to determine the local tissue tracer concentration using at least one map of the DSC MRI signal.

20. The system of claim 19, wherein the computer hardware arrangement is configured to determine the local tissue tracer concentration at least one of (i) by at least one of summing a logarithm of the DSC MRI signal over at least a portion of imaging voxels generated using the DSC MRI signal or (ii) using a lookup table.

21. The system of claim 13, wherein the computer hardware arrangement is configured to determine the AIF based on the at least one IRF by:
   determining an influx into the at least one organ based on the at least one IRF, and
   determining a cardiac output of the at least one mammal.

22. The system of claim 21, wherein the computer arrangement is configured to determine the AIF based on the at least one IRF by:
   determining a blood flow into the at least one organ based on the cardiac output, and
   determining a ratio between the influx and the blood flow.

23. The system of claim 13, wherein the computer hardware arrangement is configured to determine the at least one IRF based on the local tissue concentration by integrating the local tissue concentration across voxels of the at least one portion.

24. The system of claim 13, wherein the circulatory information includes at least one of (i) a blood volume of the at least one organ or (ii) a blood flow of the at least one organ.

25. A method for determining circulatory information regarding at least one organ of at least one mammal, comprising:
   generating at least one magnetic resonance imaging (MRI) pulse;
   applying the at least one MRI pulse to at least one portion of the at least one mammal;
   receiving at least one imaging signal from the at least one mammal that is based on the at least one MRI pulse;
   determining a local tissue tracer concentration of the at least one organ using the at least one imaging signal received from the at least one mammal, wherein the local tissue tracer concentration is based on a recirculation effect in the at least one organ;
   determining at least one impulse response function (IRF) based on the local tissue tracer concentration;
   determining an arterial input function (AIF) using the at least one IRF; and
   using a computer hardware arrangement, determining the circulatory information based on a ratio of an integrated local tissue tracer concentration and an integrated AIF.

26. The method of claim 25, wherein a numerator and a denominator of the ratio are integrated up to a time limit.

27. The method of claim 26, wherein the time limit is determined based on a particular time where the ratio stops significantly varying.

28. The method of claim 25, further comprising:
   receiving a patient-specific tracer tissue concentration time course related to a global circulatory system of the at least one mammal; and
   determining the AIF based on the patient-specific tracer tissue concentration time course by modeling a blood circulation in the global circulatory system of the at least one mammal as at least one input response function.

29. The method of claim 25, wherein the at least one organ is a brain of the at least one mammal.

30. The method of claim 25, wherein the determining of the at least one IRF is based on a non-linear parameter estimation of the local tissue tracer concentration.

31. The method of claim 25, wherein the at least one imaging signal is a dynamic susceptibility contrast (DSC)

MRI signal, and wherein the determining the local tissue tracer concentration is based on at least one map of the DSC MRI signal.

32. The method of claim 31, wherein the determining the local tissue tracer concentration includes at least one of (i) summing a logarithm of the DSC MRI signal over at least a portion of imaging voxels generated using the DSC MRI signal or (ii) using a lookup table.

33. The method of claim 25, wherein the determining the AIF based on the at least one IRF includes:
   determining an influx into the at least one organ based on the at least one IRF, and
   determining a cardiac output of the at least one mammal.

34. The method of claim 33, wherein the determining the AIF based on the at least one IRF includes:
   determining a blood flow into the at least one organ based on the cardiac output, and
   determining a ratio between the influx and the blood flow.

35. The method of claim 25, wherein the determining the at least one IRF based on the local tissue concentration includes integrating the local tissue concentration across voxels of the at least one portion.

36. The method of claim 25, wherein the circulatory information includes at least one of (i) a blood volume of the at least one organ or (ii) a blood flow of the at least one organ.

* * * * *